United States Patent
Cournoyer et al.

(10) Patent No.: US 12,304,765 B2
(45) Date of Patent: May 20, 2025

(54) METHOD AND APPARATUS FOR FOLDING A STACK OF SHEETS

(71) Applicant: Ahlstrom Oyj, Helsinki (FI)

(72) Inventors: Daniel L. Cournoyer, Windsor Locks, CT (US); Bruno Dellier, Windsor Locks, CT (US); Eric Rousset, Windsor Locks, CT (US); Philippe Sorel, Windsor Locks, CT (US)

(73) Assignee: Ahlstrom Oyj, Helsinki (FI)

( * ) Notice: Subject to any disclaimer, the term of this patent is extended or adjusted under 35 U.S.C. 154(b) by 186 days.

(21) Appl. No.: 18/011,202

(22) PCT Filed: Sep. 30, 2020

(86) PCT No.: PCT/EP2020/077338
§ 371 (c)(1),
(2) Date: Dec. 19, 2022

(87) PCT Pub. No.: WO2021/254651
PCT Pub. Date: Dec. 23, 2021

(65) Prior Publication Data
US 2023/0234805 A1    Jul. 27, 2023

Related U.S. Application Data

(60) Provisional application No. 63/040,039, filed on Jun. 17, 2020.

(51) Int. Cl.
*B65H 45/30*    (2006.01)

(52) U.S. Cl.
CPC ..... *B65H 45/30* (2013.01); *B65H 2301/4227* (2013.01); *B65H 2404/633* (2013.01); *B65H 2701/11312* (2013.01)

(58) Field of Classification Search
CPC ........ B65H 45/04; B65H 45/14; B65H 45/30; B65H 2301/4227; B65H 2403/942; B65H 2701/11312; B65H 2404/633
(Continued)

(56) References Cited

U.S. PATENT DOCUMENTS 5,564,684 A * 10/1996 Salancy ............... B65H 45/147
                                                  270/45
7,740,238 B2 * 6/2010 Iijima ...................... B42B 4/00
                                                  270/32
(Continued)

FOREIGN PATENT DOCUMENTS

| CN | 101194064 A | 6/2008 |
| CN | 105287004 A | 2/2016 |

(Continued)

OTHER PUBLICATIONS

MedPurest: Development of automatic folding mechanism for surgical drapes by medpurest. Retrieved from: https://www.medpurest.com/industrial-news/development-of-automatic-folding-mechanism-for-surgical-drapes-by-medpurest.html on Jun. 17, 2020.

*Primary Examiner* — Leslie A Nicholson, III
(74) *Attorney, Agent, or Firm* — Laine IP Oy

(57) ABSTRACT

According to an example aspect of the present invention, there is provided a method and apparatus for folding a stack of superposed sheets. The method comprises transferring the stack to a folding station, gripping a first part of the stack with a first grip and forming a crease on the stack to facilitate the folding. Then the at least a part of the stack is folded over the first part of the stack that has been gripped by utilizing the crease, the folded stack is gripped with a second grip and the folded stack is transferred from the folding station to a next handling stage and releasing the first grip.

19 Claims, 3 Drawing Sheets

(58) Field of Classification Search
USPC .................................................. 270/32, 45
See application file for complete search history.

(56) References Cited

U.S. PATENT DOCUMENTS

| | | | | |
|---|---|---|---|---|
| 7,954,797 B2* | 6/2011 | Sasahara | ................ | B65H 45/30 |
| | | | | 270/45 |
| 8,413,976 B2* | 4/2013 | Hattori | ................... | B65H 45/18 |
| | | | | 270/32 |
| 8,528,891 B2* | 9/2013 | Aiba | ...................... | B65H 45/18 |
| | | | | 270/45 |
| 8,777,830 B2* | 7/2014 | Toyoizumi | ............. | B65H 45/18 |
| | | | | 493/434 |
| 2011/0319244 A1 | 12/2011 | Toyoizumi et al. | | |

FOREIGN PATENT DOCUMENTS

| | | |
|---|---|---|
| CN | 110550279 A | 12/2019 |
| EP | 1076101 A2 | 2/2001 |
| EP | 1866225 B1 | 9/2010 |
| GB | 2298192 A | 8/1996 |
| JP | H10128000 A | 5/1988 |

* cited by examiner

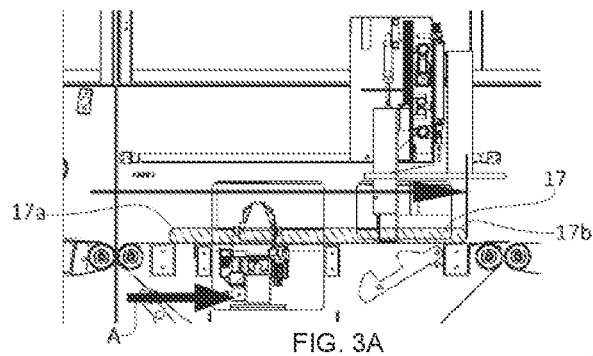
FIG. 3A
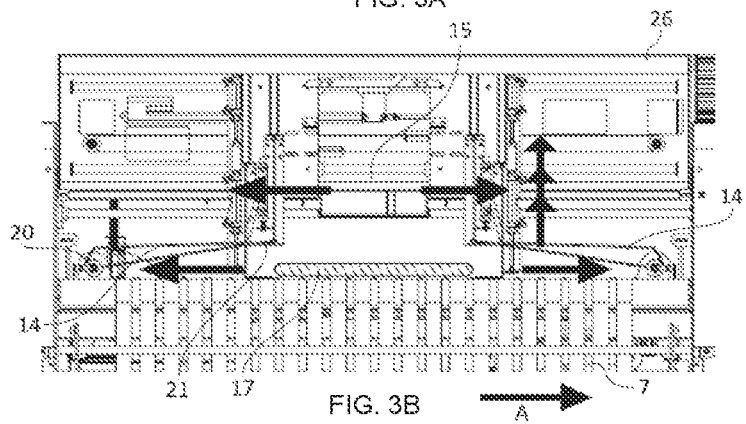
FIG. 3B
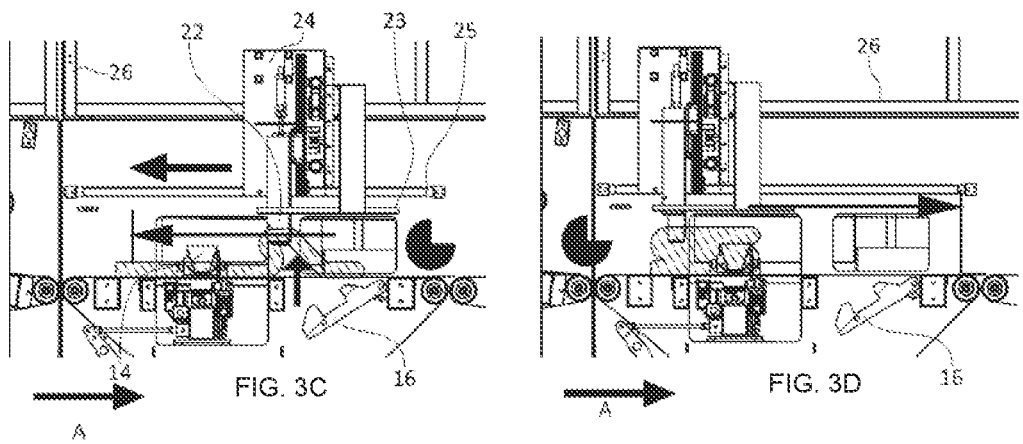
FIG. 3C
FIG. 3D

METHOD AND APPARATUS FOR FOLDING A STACK OF SHEETS

FIELD

The invention relates to packing of a stack of sheets to a transport package. Specially, the invention relates to folding a stack of sheets for packaging.

BACKGROUND

Various kinds of sheet materials are produced for different uses. In paper and board industry materials are produced in rolls and the rolled webs are cut to sheets for end use or for further converting. Typically the sheets are stacked for transport. Cellulose, paper and board sheets are often stacked on high piles and each sheet is flat in the pile. However, if the stack includes 1-250 sheets and the size of each sheet is from 750 mm×750 mm to 1500 mm×1900 mm, the height of the pile is small related to the circumferential dimensions of the sheet. Such products can be folded and packed in packages that are more convenient for transport. It has to be noted that the folding of stacks of large thin sheets is difficult at least because of the possibility of the sheets forming the stack to slide past each other. Today the folding is done manually by operators in order at least to prevent such sliding of the sheets forming the stack and also ensuring a stable folded stack. However, the efficiency of such manual folding is time consuming, expensive, ergonomically difficult for the operator and the folding quality cannot be repeatable. There are several methods and equipment for the handling of web materials, such as essentially continuous webs of plastic films, textiles, non-wovens, or papers, or the like, or of parts or pieces of such webs. These relate to modifying the movement of such webs materials, such as to allow other process steps to be performed on or with these web materials more easily. All of these relate to handling a single sheet, web or even garment or like. Some examples of known apparatuses can be found in CN 110550279, EP 1866225, CN 105287004, CN 101194064 and "Development of automatic folding mechanism for surgical drapes by medpurest" (https://www.medpurest.com/industrial-news/development-of-automatic-folding-mechanism-for-surgical-drapes-by-medpurest.html).

SUMMARY OF THE INVENTION

The invention is aimed at improving efficiency, consistency and ergonomy in folding stacks of sheets made of a paper material or a nonwoven material, and also ensuring the stability of the folded stack once formed.

The invention is defined by the features of the independent claims. Some specific embodiments are defined in the dependent claims.

In the followings some aspects of the invention are mentioned. One or more of these aspects can be used solely or in combination to realize the invention as defined in the independent claims.

According to a first aspect of the present invention, there is provided a method for folding a stack of superposed sheets, comprising
  transferring a stack to a folding station;
  gripping a first part of the stack with a first grip:
  forming a crease on the stack to facilitate the folding;
  folding at least a part of the stack over the part of the stack that has been gripped by utilizing the crease;
  gripping the folded stack with a second grip; and
  transferring the folded stack from the folding station and releasing the first grip. According to a second aspect of the present invention, there is provided an apparatus for folding a stack of superposed sheets, comprising:
  a first conveyor system for receiving a stack to a folding station;
  first gripping elements for gripping a first part of the stack with a first grip:
  a creasing element for forming a crease on the stack to facilitate the folding;
  transfer elements for folding at least a part of the stack over the part of the stack that has been gripped by utilizing the crease;
  second gripping elements for gripping the folded stack with a second grip; and
    a control sensor to perform control of transferring the folded stack from the folding station and releasing the first grip.

According to a third aspect of the invention, there is provided a method comprising forming the first grip between a first lower conveyor system and a first upper conveyor system.

According to the fourth aspect of the invention there is provided a method comprising transferring the stack on a upwards sloping part of the first lower conveyor system and forwarding the stack partially on a second upper conveyor system having an upper incoming side that is set in the same upwards tilting angle as the upwards sloping part of the first lower conveyor system.

According to the fifth aspect of the invention there is provided a method comprising forming a crease on the stack by pushing the stack to the gap between the first lower conveyor system and the second upper conveyor system.

According to the sixth aspect of the invention there is provided method wherein the stack is transferred on a second lower conveyor system, comprising forming the first grip by a set of clamps.

According to the seventh aspect of the invention there is provided method comprising forming the crease by pushing the stack upwards from the second lower conveyor system.

According to the eight aspect of the invention there is provided a method comprising folding the stack by gripping the stack at the crease and transferring at least part of the stack not gripped by the first grip over the part that is gripped by the first grip.

According to the ninth aspect of the invention there is provided a method comprising pushing the folded stack by a holding plate towards the second lower conveyor system and forwarding the second lower conveyor system and the holding plate to transfer the folded stack therebetween.

According to the tenth aspect of the invention there is provided a method wherein the first grip is formed on the trailing part of the stack and the leading part is folded at least partially on the trailing part.

According to the eleventh aspect of the invention there is provided apparatus wherein the first gripping elements for forming the first grip are a first lower conveyor system and a first upper conveyor system forming a nip.

According to the twelfth aspect of the invention there is provided an apparatus wherein the first lower conveyor system comprises an upwards sloping part for transferring the stack on of the first lower conveyor system and forwarding the stack partially on a second upper conveyor system having an upper incoming side that is set in the same upwards tilting angle as the upwards sloping part of the first lower conveyor system.

According to the thirteenth aspect of the invention there is provided an apparatus comprising a creasing bar for forming a crease on the stack by pushing the stack to the gap between the first lower conveyor system and the second upper conveyor system.

According to the fourteenth aspect of the invention there is provided an apparatus comprising a second lower conveyor system for receiving the stack and a set of clamps for forming the first grip.

According to the fifteenth aspect of the invention there is provided an apparatus comprising a creasing arm for forming the crease by pushing the stack upwards from the second lower conveyor system.

According to the sixteenth aspect of the invention there is provided an apparatus comprising transfer grip for gripping the stack at the crease and transferring at least part of the stack not gripped by the first grip over the part that is gripped by the first grip.

According to the seventeenth aspect of the invention there is provided an apparatus comprising a holding plate for pushing the folded stack towards the second lower conveyor system.

At least some aspects of the invention enable an automation of the folding of stacks of sheets and also enable an improvement of the efficiency of the manufacturing process of these stacks of sheets. Moreover, an automated method can be set up, which enables an improvement of the repeatability of the folding of the sheets and also an improvement of the further steps in the packaging process of the folded stack as all the stacks will be folded in the same manner and also have exactly the same dimensions. Moreover, an improvement in the ergonomics of the operators as they do not need to fold the stacks of sheets anymore and also contribute to prevent musculoskeletal disorders A folding machine can be accomplished that is aimed at being integrated in line in the manufacturing process and will also enable an improvement of the efficiency of the complete manufacturing process. Indeed, by using such folding machine, the folding repeatability is improved and it will also enable an improvement of the further steps in the packaging process. Moreover, this folding machine will also enable an improvement of the overall production speeds.

BRIEF DESCRIPTION OF THE DRAWINGS

FIGS. 3A-3D illustrates a folding stage in steps and in accordance with at least some embodiments of the present invention.

EMBODIMENTS

Definitions

In the present context, the term "stack" comprises a ream or a pile comprising a number of flat thin sheets of material, for example made of crepe paper, wet laid nonwoven, or spunmelt nonwoven such as for example a polypropylene spunbond-meltblown-spunbond, or a combination thereof, placed superposed on top of each other.

The present invention relates to an automatic folding machine for stack of sheets, for example a ream of sheets for sterile barrier system. Such a ream generally comprises 50 to 250 sheets of pliant flexible sheets and may be composed of single use materials like, for example, wet-laid nonwoven materials, Spunbond Meltblown Spunbond (SMS), crepe paper or any combinations thereof. The machine according to at least some embodiments of the invention is capable of folding the ream into two, three, four, five, or even six layers in the length direction while keeping the width unchanged. One of the reasons for folding the reams is to ease, refine, and optimize the delivery of the flat thin sheets of folded material. Some embodiments of the invention provide a variety of folding options depending on the ream's size and the customer's packing, boxing, and palletization needs. A key appeal of the automated line that can be composed with some embodiments of the invention is its ability to customize and tailor the folding process, all the while eliminating the need for manual folding by operators thus improving the ergonomy of this step and also preventing musculoskeletal disorders for the operators. This leads to increase in overall efficiency in handling the reams or other types of stacks. Moreover, the repeatability of the folding is improved as well as the time of this folding step, thus contributing to an improvement of the further steps in the packaging process as well as an increase of the overall production speed.

Known folding machines are dedicated to automatically folding individual sheets (albeit single or multi-layered laminated sheets), as opposed to the present invention which is capable of folding reams (reams are stacks of paper made of up to 250 individual sheets). In particular, unlike the known solutions, which serve to fold a single sheet (or multi-layered sheet—which behaves like a single sheet, since the layers are bonded together), the present invention is dedicated to folding reams (stacks of unbonded, loose individual sheets). At least some embodiments of the invention make is feasible to machine that is capable of doing so by ensuring that the sheets in the ream don't scatter or slide, and the ream doesn't shingle, spread out or unfold during folding process, as well as, during its movement throughout the line.

Figure 1:
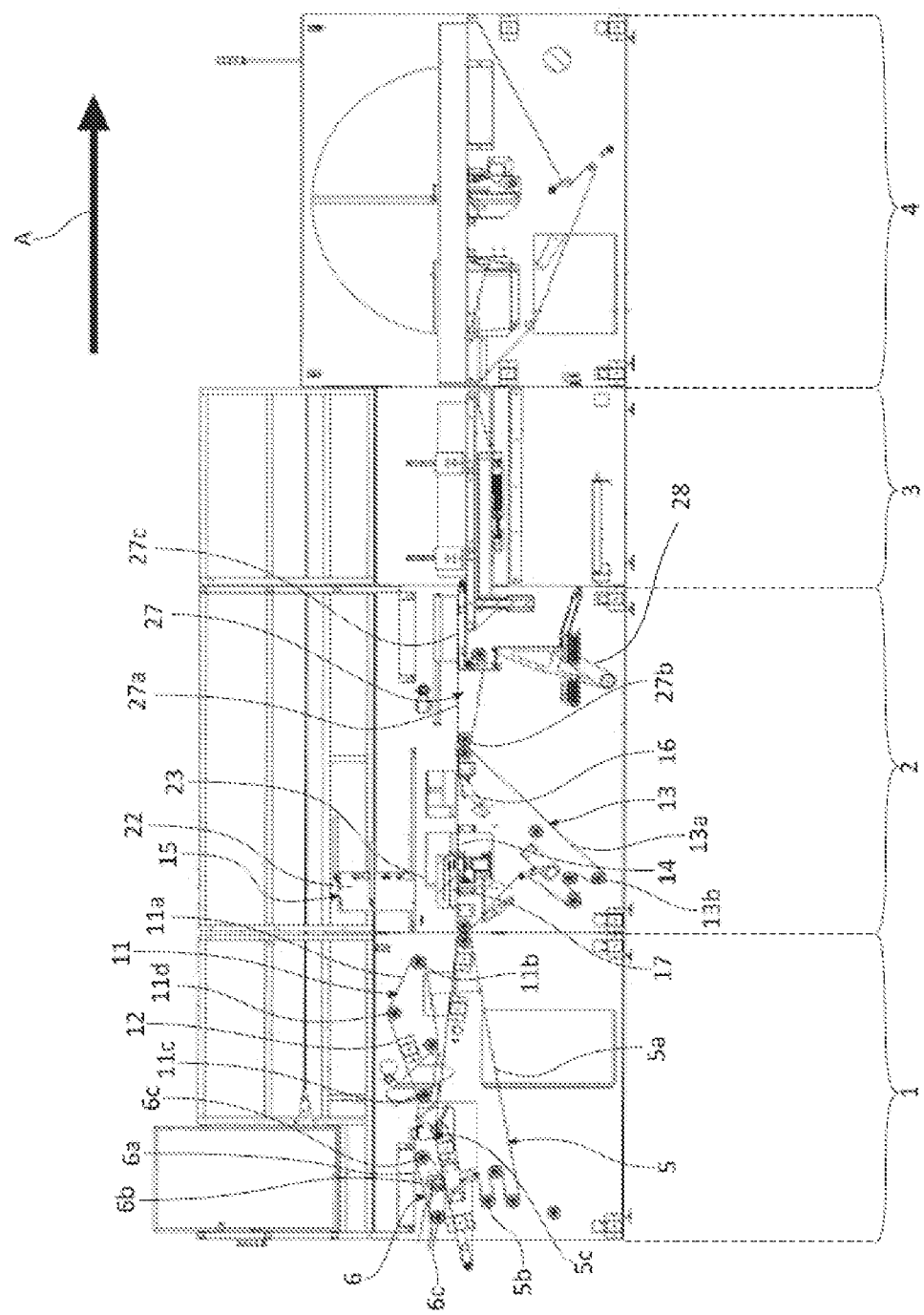
FIG. 1 illustrates a folding apparatus in accordance with at least some embodiments of the present invention.

FIG. 1 illustrates a folding line in accordance with at least some embodiments of the present invention. This folding line is designed for handling sheets for sterile barrier system. These sheets are used for wrapping sterile objects such as hospital equipment. The sheets are thin, very flexible and slippery and difficult to keep in stacks especially when the stack is moved or handled. The sheets may have a basis weight between 35 g/m$^2$ and up to 170 g/m$^2$ and a stack might be composed of up to 250 layers as a ream. The thickness of the stack before folding is usually about 50 mm, but may reach 80-100 mm in some embodiments. When folded, the thickness of the stack can be around 200 mm. This depends, of course, the number of the folds used and the number of folds done. The dimensions of sheets, and consequently the stack, are typically between 750 mm*750 mm and up to 1500 mm*1900 mm. The purpose of the folding is to fit the stack in a package. The folded materials are packed in a plastic film and in a cardboard box. Typically, the sheets folded by the folding line are made of crepe paper, wet laid nonwoven, or spunmelt material such as for example polypropylene SMS and are used as a Sterile Barrier Systems as defined in ISO 11607-1 and EN 868-2 standards that are considered as Medical Device Class I.

The receiving side of the folding line is on left side of the FIG. 1 and the delivery end is on the right side. Please see axis A in FIG. 1 indicating the travel direction. The line comprises in this lay-out three folding stages and a turning table. First in the line is a lateral folding station 1 (described in more details referring to FIGS. 2A-2D here-after), next a Z-folding station 2 (described in more details referring to FIGS. 3A-3D here-after), a turning table 3 and cross folding station 4. According to the embodiment of FIG. 1, stations 1, 2, 3 and 4, forming the folding line, are linked together via automatic moving conveyors. It has to be noted that the lateral folding station 1, the Z-folding station 2, or also the cross folding station 4 can be bypassed if the folded of the stack corresponds exclusively a Z-folded stack or a L-folded stack respectively as it will be disclosed in more details here-after.

The lateral folding station 1 comprises a first lower conveyor system 5, which is angled upwards in relation to the horizontal level so that the first lower conveyor system 5 rises as a slope in its transport direction indicated by axis A. The first lower conveyor system 5 in this example is formed of a plurality of parallel conveyor belts 5a that are spaced apart so that a slot is formed between adjacent belts 5a (see FIG. 2B). The conveyor belts 5a are arranged to run around rolls 5b, 5c in a known manner.

Still referring to FIG. 1, above the first lower conveyor system 5 is a first upper conveyor system 6. This first upper conveyor system 6 in this example is formed of a plurality of parallel conveyor belts 6a that are spaced apart so that a slot is formed between adjacent belts 6a. The conveyor belts 6a are arranged to run around rolls 6b, 6c in a known manner. The first upper conveyor system 6 is configured triangular so that one of the rolls of the first upper conveyor system 6 is a pressing roll 6b set to press the belt 6a of the first upper conveyor system 6 towards the belt 5a of the first lower conveyor system 5. Two guide rolls 6c are placed on either side of the press roll 6b for forming the triangular shape of the first upper conveyor system 6 and are guide paths for the conveyor belt 6a of the first upper conveyor system 6. In this way an incoming nip is formed between the first lower conveyor system 5 and the first upper conveyor system 6 on the incoming travel direction indicated by axis A. In use of the folding line, the stack 17 aimed at being folded is pressed between the belt 5a of the first lower conveyor system 5 and the belt 6a of the first upper conveyor system 6, said first lower conveyor system 5 and first upper conveyor system 6 are running in the direction of axis A and at the same speed in order to avoid any discrepancy between the sheets forming the stack 17. More particularly, in this example illustrated by FIG. 1, the conveyor belt 5a of the first lower conveyor system 5 is running clockwise and the conveyor belt 6a of the first upper conveyor system 6 is running counter-clockwise to enable the stack 17 to move in the travel direction (that is to say in the direction illustrated by axis A). The running directions of the conveyor belts 5a and 6a are synchronized with each other and depend on the travel direction (axis A) of the stack 17. For example, if the stack travels in opposite direction to the axis A, the conveyor belts 5a, 6a are set to run in opposite directions.

The upwards angled part of the first lower conveyor system 5 ends at an apex roll 5c and continues as a downwards angled part, forming a descending slope in the travel direction indicated by axis A. Above this downwards angled part of the first lower conveyor system 5 is a second upper conveyor system 11. The second upper conveyor system 11 in this example is formed of a plurality of parallel conveyor belts 11a that are spaced apart so that a slot is formed between adjacent conveyor belts 11a. The conveyor belts 11a are arranged to run around rolls 11b, 11c, 11d in a known manner. The second upper conveyor system 11 has an upwards tilted upper incoming side 12. This upper incoming side 12 extends between a guide roll 11c placed after the apex roll 5c in travel direction of the folding line and a guide roll 11d. The upper incoming side 12 of the second upper conveyor system 11 is set on same tilted angle as the first lower conveyor system 5. The lower part of the second upper conveyor system 11 is set towards the first lower conveyor system 5 so that a gap is formed between the conveyor belts 5a of the first lower conveyor system 5 and the conveyor belts 11a of the second upper conveyor system 11 (as it will be described in more details here-after). The first lower conveyor system 5 continues to the Z-folding station 2.

The Z-folding station 2 comprises a second lower conveyor system 13 that has an upper surface that is arranged to run horizontally. The second lower conveyor system 13 in this example is also formed of a plurality of parallel conveyor belts 13a that are spaced apart so that a slot is formed between adjacent belts. The conveyor belts 13a are arranged to run around rolls 13b in a known manner. The elements for performing the folding at Z-folding station 2 comprise of a fixed set of clamps 14, a movable set of clamps 15 and a lifting arm 16. The fixed set of clamps 14 can be automatically repositioned according to the format of the stack 17 of paper. The movable set of clamps 15 comprises transfer grips 22 and optionally a holding plate 23 (see FIG. 3C). The lifting arm 16 is a bar designed to fit between conveyor belts 13a and configured to lift up the leading edge of the stack 17 which allows the set of transfer grip 22 to go underneath the stack 17 to grab this stack 17. The operation of the Z-folding station 2 is described in more details here-after by referring to FIGS. 3A-3D. Between the Z-folding station 2 and the turning table 3, the folding line comprises a transferring conveyor system 27 having an end 27c extending horizontally to the turning table 3. The transferring conveyor system 27 in this example is formed of a plurality of parallel conveyor belts 27a that are spaced apart so that a slot is formed between adjacent belts. The conveyor belts 27a are arranged to run around rolls 27b in a known manner. The end 27c of the transferring conveyor system 27 is linked to a collapsing arm 28 configured for dropping down the folded stack 17 on the turning table 3 by collapsing the end 27c of the transferring conveyor system 27 as will be described in more detail here-after.

Next in the folding line are the turning table 3 and the cross folding station 4. During the folding process, before the folded stack 17 gets to the cross folding station 4 (the third folding station), it is passed through a turning table 3 which rotates the folded stack by 90° and maintains the position, orderliness, and stability of all the sheets in the stack. The turning table 3 in this example is formed of a plurality of parallel belts that are spaced apart so that a slot is formed between adjacent belts. The belts are arranged to run around rolls in a known manner. Optionally, the turning table 3 can comprise one or more holding arm(s) configured to maintain the stack 17 in place during the rotation of the turning table 3. Once the stack is rotated, it passes through the cross folding station 4 (the third station). At this stage, the folded ream can optionally be cross folded.

The folding line also comprises a control sensor to perform control of transferring the stack 17 during all the operation of the folding lines. Such control sensor can for example be a computer, a controller or similar apparatus normally used for automated handling and production lines or systems. More particularly, the control sensor is able to determine the position of the stack 17 all along the folding line, with optical detection devices such as cameras for example, and also pilot the stations such as for example the speed and direction of the conveyor belts 5a, 6a, 11a, 13a, 27a.

The operation of the lateral folding station 1 and the Z-folding station 2 are described below.

FIGS. 2A-2D depict schematically the lateral folding of a stack 17 of sheets and also illustrate the operation of the lateral folding station 1. A stack 17 is formed at a preceding process stage and received at the folding line on the first lower conveyor system 5. The stack 17 is transported on the first lower conveyor system 5 upwards to the nip formed of the first lower conveyor system 5 and the first upper conveyor system 6 (FIG. 1). The nip formed by the conveyor belts 5a of the first lower conveyor system 5 and the conveyor belts 6a of the first upper conveyor system 6 holds the stack 17 together so that the sheets are not separated. The stack 17 is forwarded to the second upper conveyor system 11 on its upper incoming side 12. A guide arm 19 is turned to its upper position 19a to close the gap formed between the apex point (at the apex roll 5c) of the first lower conveyor system 5 and the incoming end of the second upper conveyor system 11 at the beginning of the upper incoming side 12 of said second upper conveyor system 11. The guide arm 19 aids the incoming edge of the stack 17 over the gap between the first lower conveyor system 5 and the second upper conveyor system 11. The stack 17 is transferred partially on the upper incoming side 12 of the second upper conveyor system 11. During this step, the second conveyor system 11 illustrated on FIG. 1 runs in a clockwise direction. Now, the trailing edge of the stack forming the first part 17a of the stack 17 is held between the first lower conveyor system 5 and the first upper conveyor system 6 and the leading edge of the stack forming the second part 17b of the stack 17 is on the second upper conveyor system 11. The leading and trailing edges are determined by the travel direction of the stack 17 indicated by the axis A.

More particularly, the length of the stack transferred on the second upper conveyor system 11 depends on the number of folds of the final folded stack 17; for example 50% of the length of the stack 17 can be transferred on the upper incoming side 12 of the second upper conveyor system 11 if the folded stack 17 is aimed at presenting only two folds; in another example 25% or 75% of the length of the stack 17 can be transferred on the upper incoming side 12 of the second upper conveyor system 11 if the folded stack 17 is aimed at presenting four folds. The length of the stack 17 transferred on the upper incoming side 12 of the second upper conveyor system 11 is controlled by the control sensor and also according to the dimensions setup for example.

Once the stack 17 is partially transferred on the upper incoming side 12 of the second upper conveyor system 11, the guide arm 19 return to its original position to open the gap between the first lower conveyor system 5 and the second upper conveyor system 11. The second upper conveyor system 11 then runs in a counter-clockwise direction, the first lower conveyor system 5 and the first upper conveyor system 6 still running in a direction enabling the stack 17 to travel in the travel direction illustrated by axis A, to enable the formation of a crease of the stack 17 in the gap formed between the first lower conveyor system 5 and the second upper conveyor system 11 and also transfer the part of the stack 17 towards this gap. To help the formation of the crease, a creasing bar 18 is then pushed towards the upper surface of the stack 17 and on the gap between the first lower conveyor system 5 and the second upper conveyor system 11. According to a non-illustrated variant, the creasing bar 18 can be replaced by a pressurized air system to form the crease in the gap between the first lower conveyor system 5 and the second upper conveyor system 11. The lower surface of the stack 17 is supported by the conveyor belt 5a of the first lower conveyor system 5 and a crease is formed on the stack 17 by pushing it to the gap between the first lower conveyor system 5 and the second upper conveyor system 11 (as represented on FIGS. 2B and 2C). Simultaneously, the trailing edge of the stack 17 is held between the first lower conveyor system 5 and the first upper conveyor system 6 (not shown in FIGS. 2, but represented on FIG. 1). The first lower conveyor system 5 and the second upper conveyor system 11 feed the folded stack 17 forwards. In this folding process the stack 17 is continuously held by the nip created between the first lower conveyor system 5 and the first upper conveyor system 6 throughout the folding stage, The trailing edge is held by the first lower conveyor system 5 and the first upper conveyor system 6 and after the crease is formed, the stack 17 is transferred into the gap between the first lower conveyor system 5 and the second upper conveyor system 11 and pressed therebetween. As the stack 17 is simultaneously transferred forwards from the nip between the first lower conveyor system 5 and the first upper conveyor system 6, the pressure on the trailing edge is released and the folded stack 17 can be transported forward on the first lower conveyor system 5.

Figure 2A:
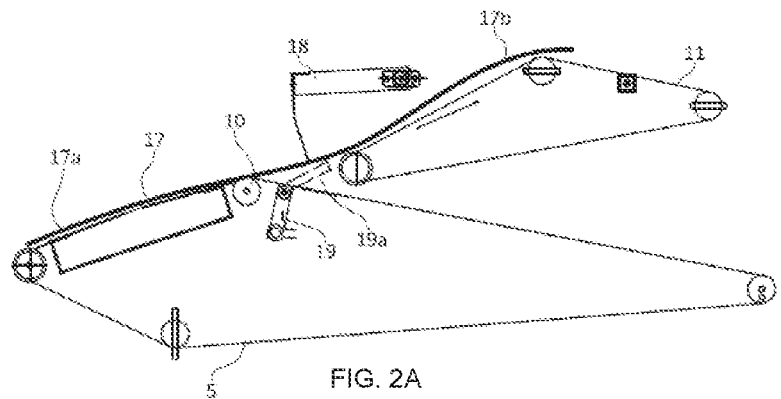
FIGS. 2A-2D illustrate a folding stage in steps and in accordance with at least some embodiments of the present invention.
Figure 2B:
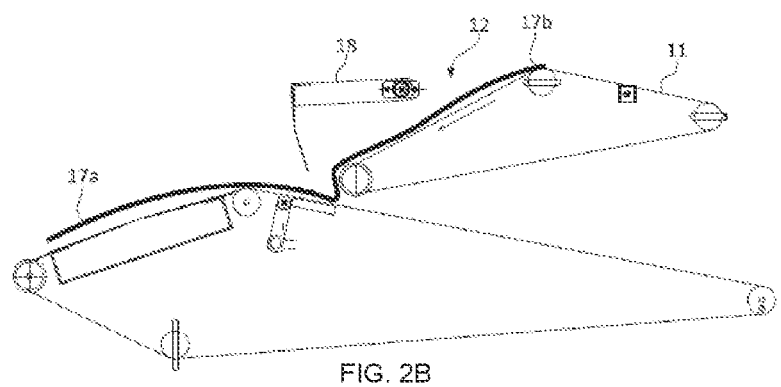
Figure 2C:
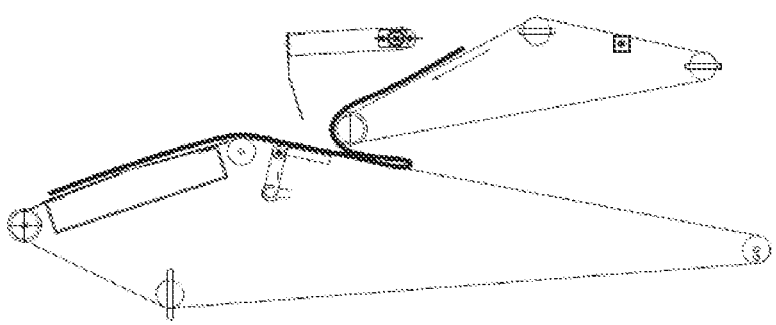
Figure 2D:
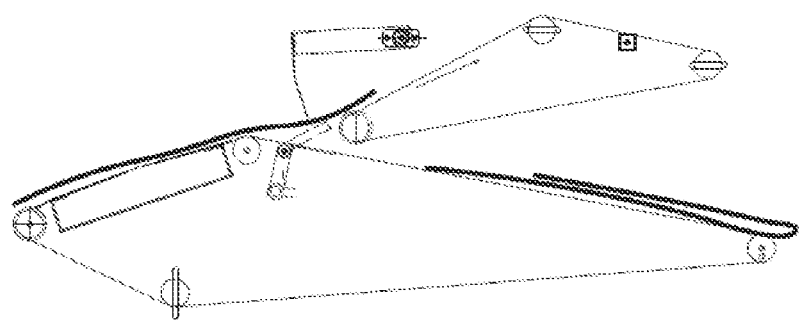

As can be seen from FIGS. 2A and 2B vs. FIGS. 2C and 2D, the above folding method allows folding the stack 17 at any place on the length of the stack 17. The crease and the fold may be made in the middle of the stack 17 as in FIGS. 2A and 2B making a symmetrically folded stack 17, or the fold may be made on any point of the stack 17 for making an asymmetrically folded stack 17 with any desired dimensions.

Moreover, it is possible that the stack 17 does not need to be folded by the lateral folding station 1. In such a case, this lateral folding station 1 can be bypassed by keeping the guide arm 19 in its original position as represented on FIGS. 2B and 2C in order to enable the stack 17 to stay on the first lower conveyor 5 without any operation of the upper incoming side 12 of the second upper conveyor 11.

FIG. 3 (3A, 3B, 3C, 3D) illustrates an example of the Z-folding station 2 and supporting at least some embodiments of the present invention. The starting position is shown in FIG. 3A. The stack 17 is transferred to the Z-folding station 2 by the first lower conveyor system 5 and moved to the second lower conveyor system 13. The stack 17 may be folded at the lateral folding station 1 or it may be an unfolded stack 17 that is folded first time at the Z-folding station 2. FIG. 3B is a side view of the starting position shown in FIG. 3A. This FIG. 3B shows also one type of conveyor suitable for accomplishing at least some embodiments of the invention. This second lower conveyor system 13 comprises a plurality of parallel conveyor belts 13a spaced apart so that slots are formed between the conveyor belts 13a. The belts 13a are arranged to run around rolls 13b. This type of belt arrangement enables manipulating the stack 17 through the slots between the conveyor belts 13a. FIG. 3B further shows a fixed set of clamps 14. In this example the fixed set of clamps 14 comprise two opposite swivel arms that are mounted on a fixed turning joint 20 at one end and have a clamping pad 21 at the opposite end. The swivel arms are positioned on sides of the second lower conveyor system 13 and extend over the second lower conveyor system 13. The fixed set of clamps 14 may be in fixed position only in relation to the transfer direction of the second lower conveyor system 13. They may be movable in crosswise direction in relation to the second lower conveyor system 13 to accommodate the gripping position of the clamping pads 21 to different sizes of stacks 17. The movement is shown by arrows in FIG. 3B.

The movable set of clamps 15a of the Z-folding station 2 comprises of transfer grips 22 and a holding plate 23. These are mounted on a manipulating unit 24 of the movable set of arm system 15. The manipulating unit 24 is mounted on rails 25 to a frame 26 of the folding line. The manipulating unit 24 is commonly used by a manipulator or a robot that provides horizontal movement of the manipulating unit 24 and the movable set of clamps 15 mounted thereto horizontally in the direction parallel to the transfer direction of the second lower conveyor system 13. It also provides vertical movement of the transfer grips 22 and the holding plate 23. Manipulators and robots for providing these movements are well known in the art and are not described in detail herein.

The Z-fold is done in the following way. First, a stack 17 is transferred to the second lower conveyor system 13 and transported with it to a desired folding position. The sideways position of the fixed set of clamps 14 is adjusted, if necessary, and the stack 17 is gripped by the fixed clamps 14 on both sides. Next, the lifting arm 16 is turned upwards between the conveyor belts 13a of the second lower conveyor system 13 to form a pocket under the leading edge of stack 17. The transfer grips 22 are inserted into this pocket on both sides of stack 17 and closed to grip stack 17. The transfer grips 22 are lifted upwards and the loose end (the part of the stack that is not held by fixed set of clamps 14) of the stack 17 is lifted and drawn backwards. Now the transfer grips 22 may be moved in the direction to the set of fixed clamps 14 by the manipulating unit 24. This horizontal movement may be adjusted so that the creasing and gripping point is placed about two thirds of the length of the stack 17 from the trailing edge of the stack 17 and the transfer grips 22 are moved towards the trailing edge so that the stack 17 is set as a double fold over the part of the stack that is held on the second lower conveyor system 13. The leading edge of the stack 17 is the set on the same line where the first fold of the stack 17 placed on the second lower conveyor system 13 is formed. The place of the lowest fold may be secured by the set of fixed clamps 14 so that the stack is turned over the edge of the clamps. This way of folding forms a neatly folded stack that is between three and six superposed layers stacked sheets in Z-form (as seen from the side of the folded stack).

After the fold is formed, the folded stack 17 is held stable by pressing the holding plate 23 over the folded stack 17. Now the second lower conveyor system 13 may be started and the stack 17 is moved forwards. The holding plate 23 and the manipulator unit 24 accelerate and maintains the same velocity as the second lower conveyor system 13 and the folded stack 17 keeping the folded stack 17 in its form.

The Z-folding station 2 further comprises the transferring conveyor 27 and the collapsing arm 28 to transfer and drop the folded stack 17 onto the turning table 3. The folded stack 17 travels on the transferring conveyor 27 while pressed by the holding plate 23. When the folded stack 17 reaches the end 27c of the transferring conveyor 27, the collapsing arm 28 begins to move the transferring conveyor system 27 in the opposite direction of the axis A. At the same time, the holding plate 23 stops pressing on the folded stack 17 and the conveyor belts 27a of the transferring conveyor system 27 continue to move in the clockwise direction thus enabling the dropping of the folded stack 17 on the turning table 3.

In both of the lateral folding method and Z-folding method the stack 17 is held (by the nip or the fixed grips) at the trailing part of the stack 17 to hold the stack 17 coherent and the leading part of the stack 17 is folded over the trailing part. As the stacks 17 are moving forwards in the line, this may be more efficient than reversing the action and folding the trailing part over the leading part. Herein the leading part is the part of the stack 17 from the leading edge to at least one crease and the trailing part is a part that extends from the trailing edge until at least one crease. the leading edge is first edge in the transfer direction and the trailing edge is the last edge in the transfer direction.

In the above described methods the folding is performed by holding the stack 17 in order to keep it together. Thereafter a crease is formed to facilitate folding of the loose part of the stack 17 at least partially over the held part of the stack 17. The stack 17 is folded and the folded stack 17 is held to keep the folded stack 17 together. In this way the stack 17 is held securely at all stages of folding (via the nip, fixed drips, and holding plate 23) and sheets of the stack 17 can't slide loose or the stacks 17 disintegrate.

A folding line that can be accomplished by at least some embodiments of the present invention may be composed of 3 different folding stations 1, 2, 4, a turning table 3, a movable cross belt and an automatic changeover which is utilized by an operator control panel. The first station, a "lateral folding" station 1, comprises a plurality of automated tools such as press rolls, sensors and a reverse folding mechanism which can all be adjusted, controlled, and customized by the operator. The second station is a "Z Folding" station 2. This Z-folding station 2 contains multiple clamps with different sizes. The bigger clamps are fixed at a particular position, while the smaller make the fold based on the operator's modifications. These clamps can be adjusted based on speed, location, and timing. By combining the "L Folding" and the "Z folding" stations, the automated line is capable of folding stacks 17 into two, three, four, five, or even six layers. Before the stack 17 gets to the third station 4, it passed through a turning table 3 which rotates the folded stack by 90 degrees and maintains the position, orderliness, and stability of all the sheets forming the folded stack 17. Once the folded stack 17 is rotated it passes through the third station 4 which is a "cross fold" station. At this stage, the folded stack 17 can optionally be cross folded. Such a folding line provides great versatility and flexibility for forming different sizes and shapes of stacks 17 for packaging.

As stated above, a machine that can be designed by using at least some embodiments of the invention is capable of folding stacks 17 of sheets of a sterile barrier system. These stacks 17 may comprise up to 250 unbonded sheets. The advantage of at least some embodiments of the invention is that they provide capability of folding these stacks 17 while avoiding pleats, tears, and shingles while maintaining equal folds of stacks of up to 250 overlapped sheets with regular gaps. The at least some embodiments enable to do this with the mechanical design of the automated line. Particularly, at the entrance of the machine the stack 17 is handled by multiple belts, both under and on top of it, that ensure its orderly assembly prior to conducting the folds. Subsequently, after the ream is folded and before it passes through the cross fold station 4, it's stabilized by a mechanical arm as it transitions into the turning table 3—this ensures the steadiness of the stack during its movement throughout the automated line. Similarly, there's another arm that holds the stack 17 in place, while it is rotated in the turning table 3.

WORKING EXAMPLES

A ream of for example 125 sheets of crepe paper with different lengths and widths as listed in the table here-after will be automatically folded into a predetermined number of layers by using the folding line described above and more particularly the L-folding station 1 and/or the Z-folding station 2 in order to have a final length to be place in a specific card box, see below:

| Length of the ream (mm) | Width of the ream (mm) | Length of the cardbox (mm) | Number of folds | Stations of the folding line used for the folding |
|---|---|---|---|---|
| 1500 | 1900 | 380 | 6 | L-folding station and Z-folding station |
| 1000 | 1000 | 380 | 3 | Z-folding station |
| 750 | 750 | 410 | 2 | L-folding station |
| 900 | 900 | 380 | 3 | Z-folding station |

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting. In particular the conveyor belts of the conveyor systems can be single belts instead of plurality of parallel belts.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

Moreover, the terms "first" and "second" used in the present description are used to differentiate elements that are close but not the same, and such terms "first" and "second" can be interverted.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

INDUSTRIAL APPLICABILITY

The invention can be utilized in handling stacks of sheets and for providing machinery for handlings stacks of sheets.

REFERENCE SIGNS LIST 1 lateral folding station
2 Z-folding station
3 turning table
4 cross folding station
5 first lower conveyor system
5a conveyor belt
5b roll
5c apex roll
6 first upper conveyor system
6a conveyor belt
6b pressing roll
6c guide roll
11 second upper conveyor system
11a conveyor belt
11b roll
11c guide roll
11d guide roll
12 upper incoming side
13 second lower conveyor system
13a conveyor belt
13b roll
14 fixed set of clamps
15 movable set of clamps
16 lifting arm
17 stack
17a first part
17b second part
18 creasing bar
19 guide arm,
19a guide arm, upper position
20 turning joint
21 clamping pad
22 transfer grips
23 holding plate
24 manipulating unit
25 rails
26 frame
27 transferring conveyor system
27a conveyor belt
27b roll
27c end
28 collapsing arm

CITATION LIST

Patent Literature

CN 110550279, EP 1866225, CN 105287004, CN 101194064

Non Patent Literature

"Development of automatic folding mechanism for surgical drapes by medpurest" (https://www.medpurest.com/industrial-news/development-of-automatic-folding-mechanism-for-surgical-drapes-by-medpurest.html)

The invention claimed is:

1. A method for folding a stack of superposed sheets, comprising:
   transferring the stack to a folding station;
   forming a first grip between a first lower conveyor system and a first upper conveyor system;
   gripping a first part of the stack with the first grip;
   transferring the stack on an upwards sloping part of the first lower conveyor system and forwarding the stack partially on a second upper conveyor system having an upper incoming side that is set in the same upwards tilting angle as the upwards sloping part of the first lower conveyor system;
   forming a crease on the stack to facilitate the folding;
   folding at least a part of the stack over the first part of the stack that has been gripped by utilizing the crease;
   gripping the folded stack with a second grip; and
   transferring the folded stack from the folding station to a next handling stage and releasing the first grip.

2. The method according to claim 1, further comprising forming a crease on the stack by pushing the stack to a gap between the first lower conveyor system and the second upper conveyor system.

3. The method according to claim 2, further comprising performing, in a sequence:
   forming the first grip between the first lower conveyor system and the first upper conveyor system,
   transferring the stack on the upwards sloping part of the first lower conveyor system and forwarding the stack partially on the second upper conveyor system having an upper incoming side that is set in the same upwards tilting angle as the upwards sloping part of the first lower conveyor system,
   forming the crease on the stack by pushing the stack to a gap between the first lower conveyor system and the second upper conveyor system, and
   thereafter reversing the second upper conveyor system and forwarding the first lower conveyor system to grip the folded stack between the first lower conveyor system and the second upper conveyor system and releasing the grip between the first lower conveyor system and the first upper conveyor system.

4. The method according to claim 1, wherein the first grip is formed on the trailing part of the stack and the leading part is folded at least partially on the trailing part.

5. An apparatus for folding a stack of superposed sheets, comprising:
   a first conveyor system for receiving the stack to a folding station;
   first gripping elements for gripping a first part of the stack with a first grip, wherein the first gripping elements for forming the first grip are a first lower conveyor system and a first upper conveyor system forming a nip, wherein the first lower conveyor system comprises an upwards sloping part for transferring the stack on the first lower conveyor system and forwarding the stack partially on a second upper conveyor system having an upper incoming side that is set in the same upwards tilting angle as the upwards sloping part of the first lower conveyor system;
   a creasing element for forming a crease on the stack to facilitate the folding;
   transfer elements for folding at least a part of the stack over the part of the stack that has been gripped by utilizing the crease;
   second gripping elements for gripping the folded stack with a second grip; and
   a control sensor to perform control of transferring the folded stack from the folding station and releasing the first grip.

6. The apparatus according to claim 5, further comprising a creasing bar for forming a crease on the stack by pushing the stack to the gap between the first lower conveyor system and the second upper conveyor system.

7. The apparatus according to claim 5, further comprising a second lower conveyor system for receiving the stack and a set of clamps for forming the first grip.

8. The apparatus according to claim 7, further comprising a creasing arm for forming the crease by pushing the stack upwards from the second lower conveyor system.

9. The apparatus according to claim 8, further comprising transfer grips for gripping the stack at the crease and transferring at least part of the stack not gripped by the first grip over the part that is gripped by the first grip.

10. The apparatus according to claim 7, further comprising a holding plate for pushing the folded stack towards the second lower conveyor system.

11. A method for folding a stack of superposed sheets, comprising:
    transferring the stack to a folding station;
    gripping a first part of the stack with a first grip;
    forming a crease on the stack to facilitate the folding;
    folding at least a part of the stack over the first part of the stack that has been gripped by utilizing the crease;
    gripping the folded stack with a second grip; and
    transferring the folded stack from the folding station to a next handling stage and releasing the first grip,
    wherein the stack is transferred on a second lower conveyor system, and comprising forming the first grip by a set of clamps.

12. The method according to claim 11, further comprising forming the crease by pushing the stack upwards from the second lower conveyor system.

13. The method according to claim 11, further comprising folding the stack by gripping the stack at the crease and transferring at least part of the stack not gripped by the first grip over the part that is gripped by the first grip by a set of clamps.

14. The method according to claim 11, comprising pushing the folded stack by a holding plate towards the second lower conveyor system and forwarding the second lower conveyor system and the holding plate to transfer the folded stack therebetween.

15. The method according to claim 11, wherein the first grip is formed on the trailing part of the stack and the leading part is folded at least partially on the trailing part.

16. An apparatus for folding a stack of superposed sheets, comprising:
    a first conveyor system for receiving the stack to a folding station;

first gripping elements for gripping a first part of the stack with a first grip;

a creasing element for forming a crease on the stack to facilitate the folding;

transfer elements for folding at least a part of the stack over the part of the stack that has been gripped by utilizing the crease;

second gripping elements for gripping the folded stack with a second grip;

a control sensor to perform control of transferring the folded stack from the folding station and releasing the first grip; and a second lower conveyor system for receiving the stack and a set of clamps for forming the first grip.

17. The apparatus according to claim 16, further comprising a creasing arm for forming the crease by pushing the stack upwards from the second lower conveyor system.

18. The apparatus according to claim 17, further comprising transfer grips for gripping the stack at the crease and transferring at least part of the stack not gripped by the first grip over the part that is gripped by the first grip.

19. The apparatus according to claim 16, further comprising a holding plate for pushing the folded stack towards the second lower conveyor system.

* * * * *